United States Patent [19]

Klein

[11] 4,184,024
[45] Jan. 15, 1980

[54] POLYURETHANES PREPARED FROM POLYOLS FROM 2,3-MORPHOLINEDIONES

[75] Inventor: Howard P. Klein, Houston, Tex.

[73] Assignee: Texaco Development Corp., White Plains, N.Y.

[21] Appl. No.: 915,043

[22] Filed: Jun. 12, 1978

Related U.S. Application Data

[60] Division of Ser. No. 830,724, Sep. 6, 1977, Pat. No. 4,118,422, which is a continuation-in-part of Ser. No. 716,610, Aug. 23, 1976, abandoned.

[51] Int. Cl.$^2$ ............... C08G 18/14; C08G 18/50
[52] U.S. Cl. .................................. 521/167; 521/902; 528/78
[58] Field of Search ............. 521/167, 902; 528/78

[56] References Cited

U.S. PATENT DOCUMENTS

| | | | |
|---|---|---|---|
| 2,373,230 | 4/1945 | De Groote | 260/561 K |
| 2,609,380 | 9/1952 | Goldstein | 260/561 K |
| 2,723,247 | 11/1955 | Harrington | 260/30.4 N |

OTHER PUBLICATIONS

Wagner et al., "Synthetic Organic Chem.", John Wiley & Sons, New York (1955), pp. 568–569.
Drefahl et al. II, Berichte 99, (1966), pp. 11–69, 73.
Drefahl et al, I, Berichte 99, (1966), pp. 2716–2717.

*Primary Examiner*—H. S. Cockeram
*Attorney, Agent, or Firm*—Carl G. Ries; Thomas H. Whaley; James L. Bailey

[57] ABSTRACT

Covers novel polyols comprising the reaction product of a 2,3-morpholinedione and a polyoxypropylene polyamine. Said polyols or alkoxylated derivatives thereof may be used in preparing polyurethane or polyisocyanurate polymers, particularly those polymers in cellular or foam form.

4 Claims, No Drawings

POLYURETHANES PREPARED FROM POLYOLS FROM 2,3-MORPHOLINEDIONES

This is a division of application Ser. No. 830,724, now U.S. Pat. No. 4,118,422, filed Sept. 6, 1977, and said application is a continuation-in-part of copending application bearing Ser. No. 716,610, filed Aug. 23, 1976, now abandoned.

BACKGROUND OF THE INVENTION

1. Field of the Invention

This invention pertains to the field of polyols. More particularly this invention relates to the use of said polyols in preparing urethane or polyisocyanurate polymers.

2. Description of the Prior Art

Polyols or polyhydroxy compounds are well known, and widely used in preparing polyurethanes. Such polyurethanes, particularly those in a cellular or foam form are prepared by reacting a polyol with a polyisocyanate in presence of a polyurethane catalyst. Optionally other ingredients such as a blowing agent are present. In order to form a polyisocyanurate one need only utilize an isocyanurate group formation catalyst which is used to trimerize the isocyanate groups to form the isocyanurate linkages. Thus, the isocyanurate polymer contains both isocyanurate groups as well as urethane linkages. Depending upon process conditions utilized rigid, flexible, semi-flexible, and semi-rigid types of polyurethane and polyisocyanurate foams may be prepared. Some main uses of the resultant foam include those of thermal insulation and as building materials and the like.

One particular polyol source is that class of compounds known as polyether polyols formed by the reaction of a polyhydric compound having from two to eight hydroxy groups with a 1,2-epoxide such as ethylene oxide, propylene oxide or a higher alkylene oxide in the presence of a basic catalyst such as aqueous sodium or potassium hydroxides. In some instances the unalkyoxylated polyhydric compound itself may be used as a polyol source in preparing polyurethanes or polyisocyanurates in elastomer or foam form.

It therefore becomes an object of the present invention to provide a new class of polyols which are simply and inexpensively prepared and may be used with equal facility in making both polyurethanes and polyisocyanurates. It is a further object of the present invention to provide polyurethane or polyisocyanurate compositions using the above polyols useful in the preparation of foams, adhesives, binders, laminates and coatings. These, and other objects of the present invention will be apparent from the specification and examples which follow.

SUMMARY OF THE INVENTION

It has been found that a useful new class of polyols may be prepared by reacting a 2,3-morpholinedione and a polyoxypropylene polyamine. Said polyols may be used per se or further reacted with an alkylene oxide to make polyols reactive with polyisocyanates to prepare polyurethane or polyisocyanurate polymers, and particularly foams of this type polymer.

DETAILED DESCRIPTION OF THE INVENTION

The polyols of the present invention are prepared by reacting a 2,3-morpholinedione with a polyoxypropylene polyamine.

The morpholinedione reactant has the following structural formula:

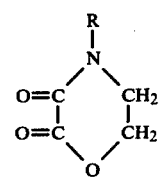

wherein R is selected from the group consisting of alkyl, cyanoalkyl, alkanol, phenyl and substituted phenyl. Where R is alkyl, cyanoalkyl, or ankanol it is preferable that the chain contain four carbons or less. Typical alkyl groups include methyl, ethyl, isopropyl, n-propyl and butyl. The same types of radicals containing one or more cyano or hydroxy groups may also be present to form the cyanoalkyl or alkanol R groups. When R is substituted phenyl, preferably it is a phenyl group substituted with one or more halo, nitro, cyano, hydroxy, or alkyl groups, particularly lower alkyl.

The above described 2,3-morpholinedione compounds may be prepared according to the procedure set out in U.S. Pat. No. 2,723,247, incorporated fully herein by reference.

Preferred 2,3-morpholinedione reactants are those which are N- or 4-substituted with hydroxyethyl, cyanoethyl, phenyl or methyl radicals.

The morpholinedione compound so provided is then reacted with a polyoxypropylene polyamine such as those described in U.S. Pat. No. 3,654,370.

Preferably, polyoxypropylene diamines of the below formula can be used as a reactant class:

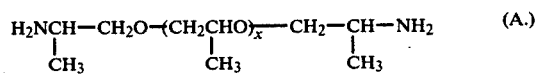

wherein x is an integer of from about 1 to 40, and polyoxypropylene triamines of the formula:

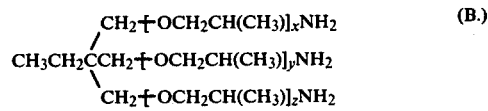

where x, y and z represent integers in the range of about 1 to 15, and the sum of x, y and z is from 3 to about 45. The preferred polyoxypropylene diamines of the formula have average molecular weights between about 190, where x is an average of 1.0 to about 2,000 where x is an average of about 32.2. Preferred polyoxypropylene triamines of the above formula have average molecular weights between about 200 to about 3,000. These polyoxypropylene di- and triamines are readily available commercially in a wide variety of molecular weight ranges, such as those sold by Jefferson Chemical Company, Inc., Houston, Tex., under the trademark JEFFAMINE ®.

Particular polyoxypropylene polyamines which can be employed are illustrated by the following two classes.

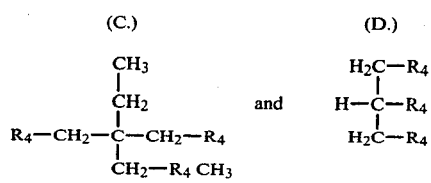

wherein $R_4$ is

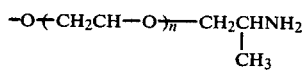

and n is 2-30.

In order to prepare the polyols of the invention one need only react the morpholinedione compound with the polyoxypropylene polyamine. Reaction may take place at room temperature, although in some cases heating may be necessary. Generally, the reaction temperature will range from about room temperature to about 150° C.; and more often ranges from room temperature to 100° C. Again, the duration of reaction may widely vary depending upon the choice of reactants, temperature of reaction, absence or presence of solvent, and other reaction parameters. Usually the reaction is considered complete in a time ranging from about 5 minutes to about 24 hours, and more often the reaction period runs from ¼ hour to 10 hours. The reactants may be so reacted without solvation. However, solvents may be employed with equal facility, and any inert solvent such as benzene, toluene, halogenated aliphatics, alcohols such as isopropanol, methanol, and ethanol, and ethers such as ethyl ether, etc., may be employed.

The ratio of the reactants may also be widely varied, and typically ranges from 1-3 moles of morpholinedione per 1-3 moles of polyamine.

The following examples illustrate preparation of typical morpholinediones which may be used as reactants here. It is to be understood that these examples are merely illustrative, and the invention is not to be limited thereto.

EXAMPLE I

Here, 4-cyanoethyl-2,3-morpholinedione was prepared.

To a 1 liter round bottom flask, fitted with a stirrer, thermometer, condenser, Dean and Stark trap and nitrogen source was added 438 grams (3 moles) of diethyl oxalate. The clear ester was heated up to about 90°-100° C. to which was added dropwise 342 grams (3 moles) of N-(2-cyanoethyl) ethanolamine. Ethanol (2 moles) formed by the condensation reaction was removed under aspirator vacuum and by resort to a vacuum at about 100° C.

The final product was a light reddish, clear, viscous liquid which was crystallized as a solid by means of hot isopropanol. The desired compound was recrystallized from methanol and had a melting point of 101°-102° C. The IR spectrum was in full agreement with its structure.

EXAMPLE II

Here, 4-phenyl-2,3-morpholinedione was prepared.

To a 500 ml. 3-necked, round bottom flask was added 146.0 grams (1.0 mole) of diethyl oxalate. The water white ester was heated up to 120° C. under nitrogen with stirring while 137 grams (1.0 mole) of N-phenyl ethanolamine was added drop-wise over a ½ hour period. The mixture was then heated to 150°-160° C. and ethanol began to collect in a trap. After heating for five hours at 160° C. under nitrogen, a total of 56.7 grams of ethanol (61.5% of theory) had been removed. The hot, yellow reaction mixture was poured into approximately 1 liter of boiling isopropanol and the product rapidly precipitated to give a solid solution. After setting approximately 72 hours the white slurry was filtered giving a light white solid. The solid was washed well with hot isopropanol and collected on a filter. The white fluffy solid was dried in a vacuum at approximately 50° C.

The first crop yield of light colorless solid was 85 grams. Another 5 grams was obtained as a second crop. The solid melted at 156°-159° C., comparing well with the literature value. The IR spectrum of this compound was consistent with the structure. The NMR spectrum confirmed the structure of the product.

EXAMPLE III

The procedure of Example I was followed with the exception that diethanolamine was utilized to prepare 4-hydroxyethyl-2,3-morpholinedione.

EXAMPLE IV

Here the procedure of Example II was followed with the exception that N-methylethanolamine was utilized as a reactant to prepare 4-methyl-2,3-morpholinedione.

The following examples illustrate typical polyols of the invention prepared by reacting a morpholinedione and a polyoxypropylene polyamine.

EXAMPLE V

To a flask, equipped with a stirrer, thermometer and nitrogen inlet was added 33.0 grams (0.28 mole) of 4-hydroxyethyl-2,3-morpholinedione (m.p. 82°-84° C.) and 89.5 grams (0.102 mole) of a polyoxypropylene diamine falling within the above formula class A where x is approximately 13. The polyoxypropylene diamine then had a molecular weight of approximately 890. A slow exothermic reaction occurred which was followed by external heating to bring the reaction mixture to 85° C., whereupon it became a homogeneous liquid. After stirring under nitrogen for 30 minutes the material was neutral to pH paper. It was subjected to high vacuum (0.2 mm.) at 85° C. to remove air and low boiling impurities. The final product was a light yellow oil having a viscosity of 31,000 cps. The product had a percent nitrogen of 4.31% which compared to a percent nitrogen calculated on the proposed structure below of 4.6%. The hydroxyl number measured was 158 whereas the hydroxyl number calculated was 186. Upon NMR spectrum analysis the structure shown below could be proposed.

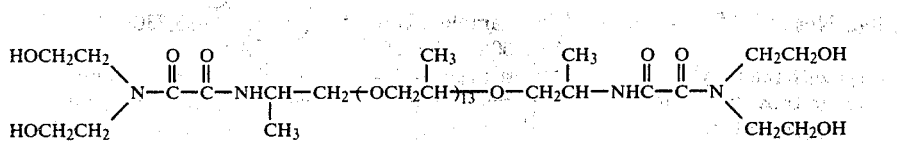

EXAMPLE VI

To a 500 ml. round bottom flask, fitted with a stirrer, thermometer and nitrogen source was added 38 grams (0.20 mole) of 4-phenyl-2,3-morpholinedione and 200 grams (0.069 mole) of a polyoxypropylene triamine falling within structure C above wherein n is approximately 20. The triamine then had an approximate molecular weight of 3000. The mixture was heated up slowly under nitrogen to 100°–105° C. and stirred for 1–2 hours, after which time the mixture became homogenous and was no longer basic to pH paper. The material was then vacuum stripped to yield 226 grams of a viscous, off-white, cloudy liquid. The material was neutral to pH paper. As analyzed the product had a hydroxyl number of about 38.2, a total amine content of 0.62, a viscosity of 64,000 cps, a percent nitrogen of 2.44 and a weight percent water of 0.055.

EXAMPLE VII

To a 500 ml. flask equipped as in Example VI was added 26.9 grams (0.207 mole) of 4-methyl-2,3-morpholinedione and 200 grams (0.069 mole) of polyoxypropylene triamine falling within structure D above where n is approximately 20. The triamine had an approximate molecular weight of 3000. The resultant slurry was stirred and heated under nitrogen to approximately 90° C. for one hour. After this time the reaction was considered complete. However, to insure final completion of reaction, heating at 100° C. for ½ hour was effected. The final product was a clear, slightly off-white mobile liquid, and was achieved in a yield of 220 grams. After vacuum stripping at 100° C. by means of an aspirator the clear material was then analyzed. The product had a hydroxyl number of 50.5, a total amine content of 0.20, a viscosity of 7,300 cps, a Gardner color of 1, a weight percent water of 0.062 and a percent nitrogen of 2.53.

EXAMPLE VIII

To a 500 ml. round bottom flask, fitted with stirrer, thermometer and nitrogen inlet was added 84.4 grams (0.5 mole) of 4-cyanoethylmorpholine-2,3-dione and 225 grams (0.25 mole) of a polyoxypropylene diamine falling within Formula A above such that the diamine had an approximate molecular weight of 890. The resultant mixture was heated at 80°–90° C. for 3 hours, then vacuum stripped at 90° C. and cooled. The final product was a clear, light reddish brown liquid that was almost neutral to pH paper and was obtained in an amount of 303 grams. The product had a hydroxyl number of 77.2 (calculated 91.5) a total amine content of 0.067 (calculated as 0.1) a viscosity of 18,750 cps and a weight percent water of 0.039.

The proposed structure of this product is as follows:

EXAMPLE IX

To a 500 ml. round bottom flask fitted with a stirrer, gas inlet, and thermometer was added 40.0 grams (0.31 mole) of 4-methyl-2,3-diketomorpholine (mp. 98°–100° C.) and 300.0 grams (0.15 mole) of a polyoxypropylene diamine falling within structure A above such that the diamine had a molecular weight of 2000. A noticeable exothermic reaction was not observed so the resultant slurry was heated on a mantle while a stream of nitrogen was passed over the reaction mixture. After heating for 1 hour at 100° C. a clear, light yellow product mixture was obtained which was slightly basic to pH paper. 2.0 grams (0.015 mole) of additional diketomorpholine was added and further reacted with the diamine present for an additional hour at 100° C. The product was a viscous light yellow liquid which was neutral to pH paper, and was obtained in the yield of 340 grams.

The product analyzed as follows:

Percent nitrogen 2.63 (percent N calc=2.48); hydroxyl number 50.8 (hydroxyl number calc=49.6); total amine content—0.07; Brookfield viscosity at 25° C.–2900 cps; Gardner color—2–3; and percent water—0.092.

The above polyols can also be derivatized by addition of alkylene oxides thereto. Thus, the just described polyols act as a suitable polyhydric initiator to which can be added the alkylene oxide or mixture of alkylene oxides to form polyether polyols.

Any of the above polyhydric compounds or mixtures of these compounds may be reacted with alkylene oxides to form the polyether polyols. The alkylene oxides which may be employed as reactants alone or as mixtures include ethylene oxide, propylene oxide, the isomeric normal butylene oxides, hexylene oxide, octylene oxide, dodecene oxide, methoxy and other alkoxy propylene oxides, styrene oxide and cyclohexene oxide. Halogenated alkylene oxides may also be used, such as epichlorohydrin, epiiodohydrin, epibromohydrin, 3,3-dichloropropylene oxide, 3-chloro-1,2-epoxypropane, 3-chloro-1,2-epoxybutane, 1-chloro-2,3-epoxybutane, 3,4-dichloro-1,2-epoxybutane, 1,4 dichloro-2,3-epoxybutane, 1-chloro-2,3-epoxybutane, and 3,3,3-trichloropropylene oxide. Generally the alkylene oxide used will contain from 2 up to 18 carbon atoms. The final polyether polyols usually will have a molecular weight ranging from about 200 to about 20,000, and more often have a molecular weight of 300–10,000.

When mixed oxides are used, they may be added to the polyhydric initiator either sequentially to form block polyether polyols as described in U.S. Pat. No. 3,535,307 or may be mixed and reacted simultaneously to form a random, or heteric oxyalkylene chain. If desired, terminal primary hydroxyl groups can be achieved by reacting ethylene oxide in a last step as

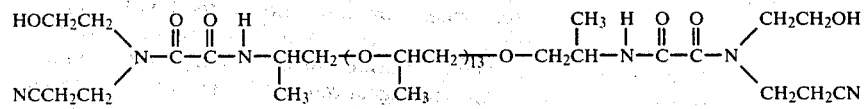

described, for example, in U.S. Pat. Nos. 3,535,307 or 3,336,242.

The reaction of the alkylene oxides with the polyhydric initiators made here is well known to those skilled in the art and occurs under basic conditions established through the use of alkali metals, their hydroxides, oxides and hydrides and in some cases basic amines.

The molecular weight of the polyether polyols can be determined by analysis for hydroxyl number which is proportional to the hydroxyl concentration per unit weight. The hydroxyl number is defined in terms of KOH equivalent per gram of alkylene oxide-initiator reaction product and is determined using well known methods. The equivalent weight, of course, bears a relationship to the molecular weight based upon the number of hydroxyl groups in the molecule and is determined from the hydroxyl number by using the following formula:

$$\text{Eq. } W = \frac{56.1 \times 1000}{\text{OH No.}}$$

In like manner the hydroxyl number as determined by the well known KOH titration, can be used to readily calculate the molecular weight using the following well known formula:

$$MW = \frac{\text{Functionality} \times 1000 \times 56.1}{\text{OH No.}}$$

The polyhydric compounds described above as prepared from the morpholinedione reactant or polyether polyols prepared therefrom may be used to make polyurethanes and polyisocyanurates, both in elastomer and foam form. When one wishes to prepare a polyurethane a conventional urethane formation catalyst is employed along with the polyols here, and an aromatic polyisocyanate and optionally other ingredients such as a blowing agent. To form the polyisocyanurate polymer an isocyanurate group formation catalyst is used to trimerize the isocyanate groups to form the isocyanurate linkages.

Any aromatic polyisocyanate may be used to prepare polyurethanes or polyisocyanurates by reaction with the polyols described here. Typical aromatic polyisocyanates include m-phenylene diisocyanate, p-phenylene diisocyanate, polymethylene polyphenylisocyanate, 2,4-toluene diisocyanate, 2,6-toluene diisocyanate, dianisidine diisocyanate, naphthalene-1,4-diisocyanate, diphenyl-4,4'diisocyanate, aliphatic-aromatic diisocyanates, such as xylylene-1,4-diisocyanate, xylylene-1,2-diisocyanate, xylylene-1,3-diisocyanate, bis(4-isocyanatophenyl) methane, bis(3-methyl-4-isocyanatophenyl) methane, and 4,4'-diphenylpropane diisocyanate.

Another group of aromatic polyisocyanates that may be used are methylene-bridged polyphenyl polyisocyanate mixtures which have a functionality of from about 2 to about 4. These latter isocyanate compounds are generally produced by the phosgenation of corresponding methylene-bridged polyphenyl polyamines, which are conventionally produced by the reaction of formaldehyde and primary aromatic amines, such as aniline, in the presence of hydrochloric acid and/or other acidic catalysts. Known processes for preparing the methylene-bridged polyphenyl polyamines and corresponding methylene-bridged polyphenyl polyisocyanates therefrom are described in the literature and in many patents, for example, U.S. Pat. Nos. 2,683,730; 2,950,263; 3,012,008; 3,344,162; and 3,362,979.

Most preferred methylene-bridged polyphenyl polyisocyanate mixtures used here contain from about 20 to about 100 weight percent methylene diphenyldiisocyanate isomers with the remainder being polymethylene polyphenyl diisocyanates having higher functionalities and higher molecular weights. Typical of these are polyphenyl polyisocyanate mixtures containing about 20 to 100 weight percent methylene diphenyldiisocyanate isomers, of which 20 to about 95 weight percent thereof is the 4,4'-isomer with the remainder being polymethylene polyphenyl polyisocyanates of higher molecular weight and functionality that have an average functionality of from about 2.1 to about 3.5. The isocyanate mixtures are known commercially available materials and can be prepared by the process described in U.S. Pat. No. 3,362,979 issued Jan. 9, 1968 to Floyd E. Bentley.

The amount of polyol compound to be used relative to the isocyanate compound normally should be such that the isocyanate groups are present in at least an equivalent amount, and preferably, in slight excess compared with the free hydroxyl groups. Preferably, the ingredients will be proportioned so as to provide from about 1.05 to about 1.5 mole equivalents of isocyanate groups per mole equivalent of hydroxyl groups.

A catalyst, of course, is also used in preparing the polyurethanes by the reaction of the above polyisocyanates or others, and the polyols described here. The catalyst is usually employed in the amount of from about 0.05 to about 4.0 weight percent based on the combined weight of the polyol and polyisocyanate. More often the amount of catalyst used is 0.1–1.0 weight percent.

Typical polyurethane catalysts are tertiary amines, organic tin compounds or other polyurethane catalyst or mixtures thereof. The organic tin compound particularly useful in making flexible foams may suitably be a stannous or stannic compound, such as a stannous salt of a carboxylic acid, a trialkyltin oxide, a dialkyltin dihalide, a dialkyltin oxide, etc., wherein the organic groups of the organic portion of the tin compound are hydrocarbon groups containing from 1 to 8 carbon atoms. For example, dibutyltin dilaurate, dibutyltin diacetate, diethyltin diacetate, dihexyltin diacetate, di-2-ethylhexyltin oxide, dioctyltin dioxide, stannous octoate, stannous oleate, etc., or a mixture thereof, may be used.

Tertiary amines include triethylene diamine, trialkylamines (e.g. trimethylamine, triethylamine), trialkylamines (e.g. trimethylamine, triethylamine), heterocyclic amines, such as N-alkylmorpholines (e.g., N-methylmorpholine, N-ethylmorpholine, etc.), 1,4-dimethylpiperazine, triethylenediamine, etc., and aliphatic polyamines, such as N,N,N'N'-tetramethyl-1,3-butanediamine.

Both polyurethane coatings or elastomers and foams may be produced here. Depending upon the choice of reactants, and reaction conditions, one may prepare rigid, flexible, semi-rigid and semiflexible foams. Usually an extraneous blowing agent, such as a halogenated, normally liquid hydrocarbon, carbon dioxide, etc., is employed if foam is to be generated.

As further examples, halogenated low-boiling hydrocarbons, such as trichloromonofluoromethane and methylene chloride, nitrogen, etc., may be used. The inert blowing agent reduces the amount of excess isocyanate and water that is required in preparing flexible urethane foam. For a rigid foam, it is preferable to avoid the use of water and to use exclusively the extraneous blowing agent. Selection of the proper blowing agent is well within the knowledge of those skilled in the art. See for example U.S. Pat. No. 3,072,082.

The amount of blowing agent used will vary with the density desired in the foam product. In general, it may be stated that for 100 grams of reaction mixture containing an average isocyanate/reactive hydrogen ratio of about 1:1, about 0.005 to 0.3 mole of gas is used to provide densities ranging from 30 to 1 pounds per cubic foot respectively.

If one desires to prepare an isocyanurate polymer an isocyanurate group formation catalyst or catalysts is employed to promote trimerization. These catalysts may be chosen from a variety of known materials.

Such catalysts include strong bases, alkali metal salts of carboxylic acids, nonbasic metal salts of carboxylic acids and aliphatic tertiary amines. For example, suitable strong bases include quaternary ammonium hydroxide, alkali metal hydroxide, and alkali metal alkoxides. Suitable alkali metal salts of carboxylic acids include, for example, sodium acetate, potassium octoate, potassium acetate, sodium benzoate, and the like. Examples of suitable tertiary amines are N,N'-diethylpiperazine, N,N'-dimethylpiperazine, trialkylamines such as trimethylamine, triethylenediamine, 2,4,6-tris(dimethylaminomethyl)phenol, and N,N',N''-tris(dimethyl 3-aminopropyl)-s-hexhydrotriazine and the like.

Furthermore, fillers can be employed in the preparation of coatings, elastomers or foams, if desired in amounts within the range of about 0.1 to about 20 weight percent. Any conventional filler known in the art can be employed, such as hydrated alumina, polyethylene, aluminum powder, and various clays and talcs.

An emulsifier or stabilizing agent may also be used in the preparation of polyurethane of polyisocyanurate foams of this invention including, for example, sulfonate castor oil or the like. One preferred foam stabilizer is that based on silicone such as, for example, a polydimethyl siloxane or a polyoxyalkylene block copolymer of a silane. The latter type of silicone oil is disclosed in U.S. Pat. No. 2,834,748. Other surfactants or emulsifying or dispersing agents which may be used include ethylene oxide modified sorbitan, or monopalmitate or ethylene oxide modified polypropylene ether glycol.

In addition to the polyols of the invention here any conventional polyol such as a polyether or polyester polyol may also be used as an additional component in making polyurethane or polyisocyanurate polymers in solid or cellular form.

Illustrative of these additional polyols one can mention the following types:

(a) polyoxyalkylene polyols including the adducts of alkylene oxides with, for example, water, ethylene glycol, diethylene glycol, propylene glycol, dipropylene glycol, glycerol, 1,2,6-hexanetriol, 1,1,1-trimethylolethane, 1,1,1-trimethylolpropane, pentaerythritol, sorbitol, sucrose, lactose, alphamethylglucoside, alphahydroxyalkylglucoside, ammonia, triethanolamine, triisopropanolamine, ethylenediamine, diethylenetriamine, novolac resins, phosphoric acid, benzenephosphoric acid, polyphosphoric acids such as tripolyphosphoric acid and tetrapolyphosphoric acid, phenol-aniline-formaldehyde ternary condensation products, aniline-formaldehyde condensation products and the like. The alkylene oxides employed in producing the polyoxyalkylene polyols normally have from 2 to 4 carbon atoms. Propylene oxide, ethylene oxide and mixtures of propylene oxide with ethylene oxide are preferred. It is known that random or block structures can be obtained depending upon the particular known procedures used for their preparation.

(b) Polyesters of polyhydric alcohols and polycarboxylic acids such as those prepared by the reaction of an excess of ethylene glycol, propylene glycol, 1,1,1-trimethylolpropane, glycerol, or the like, with phthalic acid, adipic acid, and the like.

(c) Lactone polyols prepared by reacting a lactone such as epsilon-caprolactone or a mixture of epsilon-caprolactone and an alkylene oxide with a polyfunctional initiator such as a polyhydric alcohol, an amine, or an amino-alcohol.

(d) Phosphorus-containing derivatives such as tris (dipropylene) glycol phosphite and other phosphites.

(e) The polymer/polyols produced by the in situ polymerization of a vinyl monomer in a polyol, as disclosed in U.S. Pat. Nos. 3,304,273; 3,383,351 and 3,523,093.

If desirable, the foams of the invention can be formulated to include flame retardant components to improve the fire retardancy of the foams. Any known fire retardant component compatible with rigid isocyanurate foams can be employed. This would include both the reactive and additive type fire retardants. Representatives of the additive types include halogenated organic phosphates such as tris(chloroethyl)phosphate, tris(2,3-dibromopropyl)phosphate, triphenyl phosphite, diammonium phosphate, and antimony oxide. Representatives of the chemically bound types are diethyl-N,N'-bis(2-hydroxyethyl)aminomethyl phosphonate, chlorendic acid derivatives, and phosphorous-containing polyols. When employed, the fire retardant component is added to the above-described isocyanate mixture with some other component or as a preformed mixture with some other component described hereinbefore, in an amount of about 1 to about 20 weight percent of the total foam formulation.

In preparing a flexible foam, the ingredients may be simultaneously, intimately mixed with each other by the so-called "one-shot" method to provide a foam by a one-step process. In this instance, water should comprise at least a part (e.g., 10% to 100%) of the blowing agent. This method is known to those skilled in the art, as evidenced by the following publication: duPont Foam Bulletin, "Evaluation of Some Polyols in One-Shot Resilient Foams", Mar. 22, 1960.

When it is desired to prepare rigid foams, both the "one-shot" method or the so-called "quasi-prepolymer method" may be employed, wherein the hydroxyl-containing component preferably contains from about 4 to 7 reactive hydroxyl groups, on the average, per molecule.

In accordance with the "quasi-prepolymer method", a portion of the hydroxyl-containing component is reacted in the absence of a catalyst with the polyisocyanate component in proportions so as to provide from about 20 percent to about 40 percent of free isocyanato groups in the reaction product, based on the polyol. To prepare a foam, the remaining portion of the polyol is added and the two components are allowed to react in the presence of catalytic systems such as those discussed above and other appropriate additives, such as blowing agents, foam stabilizing agents, fire retardants, etc. The blowing agent (e.g., a halogenated lower aliphatic hydrocarbon), the foam-stabilizing agent, the fire retardant, etc., may be added to either the prepolymer or remaining polyol, or both, prior to the mixing of the component, whereby at the end of the reaction a rigid polyurethane foam is provided.

Urethane elastomers and coatings may be prepared also by known techniques in accordance with the present invention wherein a tertiary amine of this invention is used as a catalyst. See, for example, duPont Bulletin PB-2, by Remintong and Lorenz, entitled "The Chemistry of Urethane Coatings".

EXAMPLE X

Here 31 grams (85 parts) of the tetraol of Example V, 5.4 grams (15 parts) of a diol formed as the reaction product of ethylene carbonate and monoethanolamine, 1.0 gram (2.8 parts) of tetramethyl propanediamine, and 5.4 grams (15 parts) of trichlorofluoromethane blowing agent were mixed well, to which mixture was added 23.7 grams (65.8 parts) of a methylene-bridged polyphenyl polyisocyanate mixture having a functionality of about 2.1. The resultant mixture was stirred well, and in about 10 seconds it began to rise as a foam. In 1 minute the material was a tack-free, rigid foam that hardened upon standing. The foam remained strong and appeared to have good dimensional stability.

The invention is hereby claimed as follows:

1. A polymer containing recurring urethane linkages, which polymer comprises the reaction product of an aromatic polyisocyanate and a polyol comprising the reaction product of a 2,3-morpholinedione and a polyoxypropylene polyamine, said morpholinedione reactant having the following structural formula:

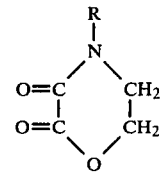

where R is selected from the group consisting of alkyl, cyanoalkyl, alkanol, phenyl and substituted phenyl.

2. The polymer of claim 1 which also contains isocyanurate linkages.

3. A cellular polymer containing recurring urethane linkages which polymer comprises the reaction product obtained by bringing together in the presence of a blowing agent and a urethane catalyst an aromatic polyisocyanate and the polyol of claim 1.

4. The cellular polymer of claim 3 which also contains isocyanurate linkages.

* * * * *